(12) United States Patent
Foat et al.

(10) Patent No.: US 9,807,979 B2
(45) Date of Patent: Nov. 7, 2017

(54) EXPLOSIVE AND NARCOTICS DETECTION DOG TRAINING WITH VAPOUR OR AEROSOL AIR IMPREGNATION

(75) Inventors: Timothy Graham Foat, Salisbury (GB); Steven Walker, Salisbury (GB); Christopher Coffey, Salisbury (GB); Matthew Brookes, Salisbury (GB)

(73) Assignee: The Secretary of State for Defence, Salisbury, Wiltshire (GB)

( * ) Notice: Subject to any disclaimer, the term of this patent is extended or adjusted under 35 U.S.C. 154(b) by 909 days.

(21) Appl. No.: 14/342,396

(22) PCT Filed: Aug. 30, 2012

(86) PCT No.: PCT/GB2012/000692
§ 371 (c)(1),
(2), (4) Date: Nov. 14, 2014

(87) PCT Pub. No.: WO2013/030525
PCT Pub. Date: Mar. 7, 2013

(65) Prior Publication Data
US 2015/0056913 A1    Feb. 26, 2015

(30) Foreign Application Priority Data

Sep. 3, 2011 (GB) .................................. 1115228.7

(51) Int. Cl.
*A62C 5/02*    (2006.01)
*A01K 15/02*    (2006.01)
(Continued)

(52) U.S. Cl.
CPC .............. *A01K 15/02* (2013.01); *A01G 25/02* (2013.01); *A61L 9/12* (2013.01); *A61L 9/122* (2013.01);
(Continued)

(58) Field of Classification Search
CPC .......... A01K 15/02; F24F 7/04; F41H 11/132; G01N 33/057; G01N 33/0006;
(Continued)

(56) References Cited

U.S. PATENT DOCUMENTS 5,728,927 A    3/1998 Ong
6,722,182 B1    4/2004 Buettner
(Continued)

FOREIGN PATENT DOCUMENTS

DE    4105163 A1    8/1992
FR    2956211 A2    8/2011
(Continued)

OTHER PUBLICATIONS

Combined Search and Examination Report dated Nov. 30, 2012 in Application No. GB1215346.6.
(Continued)

*Primary Examiner* — Steven J Ganey
(74) *Attorney, Agent, or Firm* — Kilpatrick Townsend & Stockton LLP; Dean W. Russell

(57) ABSTRACT

The present invention provides devices and methods for the impregnation of air with the vapor or aerosol of a substance in a 'controllable manner to enable the testing or training of detection means to evaluate and quantify the presence of the substance in an enclosed volume, and in• particular to enable production of training aids and quality assurance test items for use in canine-olfaction based security screening.

12 Claims, 7 Drawing Sheets

(51) Int. Cl.
  *G01N 33/00* (2006.01)
  *B05B 7/04* (2006.01)
  *B05B 7/08* (2006.01)
  *A01G 25/02* (2006.01)
  *B01J 19/00* (2006.01)
  *A61L 9/12* (2006.01)
  *F41H 11/132* (2011.01)
  *F24F 7/04* (2006.01)
  *G01N 1/02* (2006.01)
  *G01N 1/28* (2006.01)

(52) U.S. Cl.
  CPC ............. *B01J 19/0046* (2013.01); *B05B 7/04* (2013.01); *B05B 7/0815* (2013.01); *F24F 7/04* (2013.01); *F41H 11/132* (2013.01); *G01N 33/0006* (2013.01); *G01N 33/0057* (2013.01); *G01N 2001/022* (2013.01); *G01N 2001/2893* (2013.01)

(58) Field of Classification Search
  CPC ...... G01N 2001/022; G01N 2001/2893; B05B 7/0815; B05B 7/04; A01G 25/02; B01J 19/0046; A61L 9/12; A61L 9/122
  USPC ........ 239/1, 8, 145, 398, 418, 419; 119/712; 73/1.02, 1.03, 1.06; 422/68.1, 123, 124
  See application file for complete search history.

(56) References Cited

U.S. PATENT DOCUMENTS

| | | | |
|---|---|---|---|
| 2001/0047771 A1* | 12/2001 | Bulanda | A01K 15/02 119/712 |
| 2004/0202574 A1 | 10/2004 | Sapir et al. | |
| 2005/0084413 A1 | 4/2005 | Stanley, III | |
| 2006/0174843 A1* | 8/2006 | Poyner | A01K 15/027 119/712 |
| 2007/0075159 A1 | 4/2007 | Lin | |
| 2008/0295783 A1* | 12/2008 | Furton | F41H 11/132 119/712 |
| 2009/0065601 A1 | 3/2009 | Lee | |
| 2009/0077908 A1 | 3/2009 | Brasfield | |
| 2010/0242962 A1 | 9/2010 | Chen et al. | |

FOREIGN PATENT DOCUMENTS

| | | |
|---|---|---|
| GB | 1001854 A | 8/1965 |
| JP | 2000005315 A | 1/2000 |
| WO | 200109600 A1 | 2/2001 |
| WO | 2003090826 A1 | 11/2003 |
| WO | 2007054604 A1 | 5/2007 |
| WO | 2009064427 A1 | 5/2009 |

OTHER PUBLICATIONS

International Search Report dated Nov. 29, 2012 in Application No. PCT/GB2012/000692.

International Preliminary Report on Patentability dated Mar. 13, 2014 in Application No. PCT/GB2012/000692.

Search Report dated Dec. 16, 2011 in Application No. GB1115228.7.

* cited by examiner

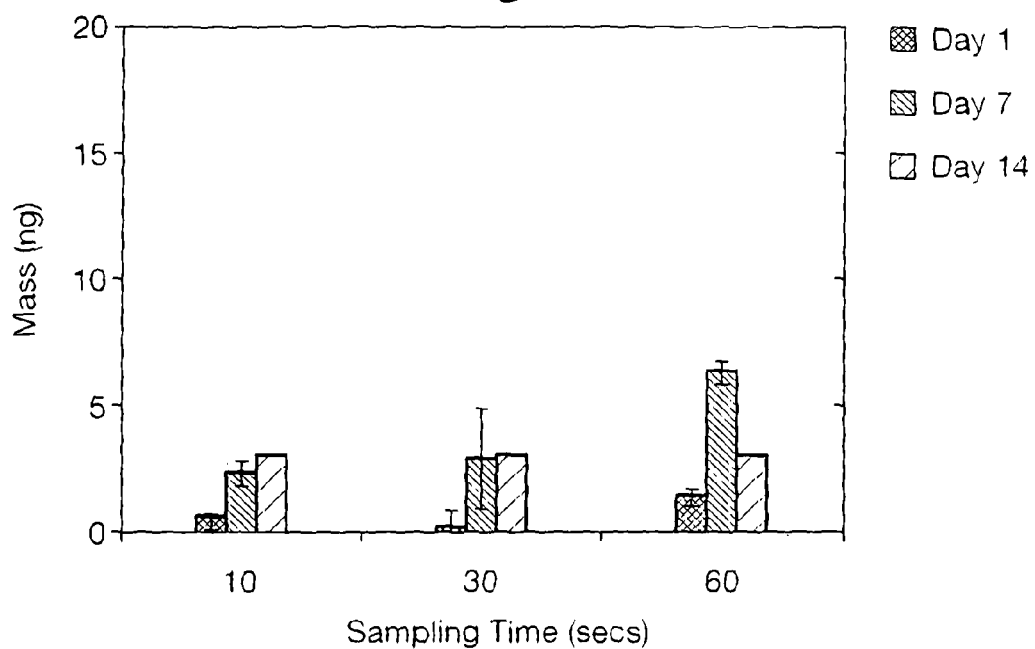
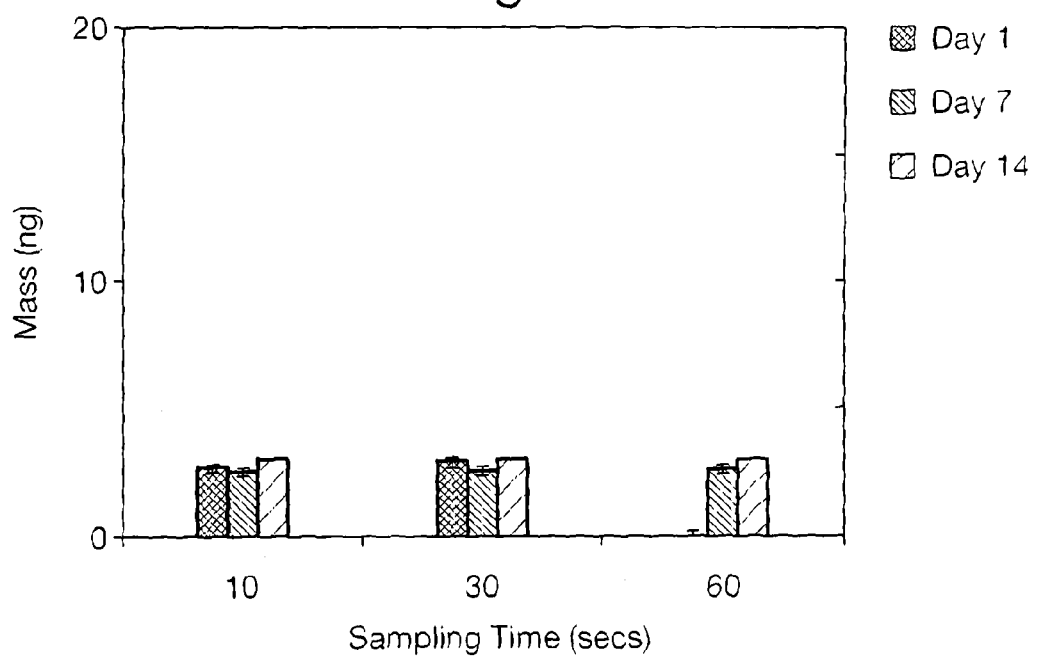

EXPLOSIVE AND NARCOTICS DETECTION DOG TRAINING WITH VAPOUR OR AEROSOL AIR IMPREGNATION

CROSS REFERENCE TO RELATED APPLICATIONS

This application is the U.S. national phase of International Application No. PCT/GB2012/000692 filed on Aug. 30, 2012, and published in English on Mar. 7, 2013 as International Publication No. WO 2012/030525 A1, which application claims priority to Great Britain Patent Application No. 1115228.7 filed on Sep. 3, 2011, the contents of both of which are incorporated herein by reference.

The present invention is concerned with devices and methods for the impregnation of air with the vapour or aerosol of a substance in a controllable manner to enable the testing or training of detection means to evaluate and quantify the presence of the substance in an enclosed volume in a real environment, and in particular to enable production of training aids and quality assurance test items for use in canine-olfaction based security screening.

There is a world-wide requirement for devices and techniques to enable the effective screening of enclosed volumes in real environments for the presence of contraband bulk material, for example identification and detection of explosives or drugs in cargo freight. X-ray techniques may be used but are ineffective if the cargo is too large or too dense. One means of detecting the presence of contraband bulk material is to analyse air sampled from the enclosed volume for the presence of vapours or aerosols emitted by the contraband material. A highly sensitive detector is required; REST (Remote Explosives Scent Tracing) uses trained sniffer dogs, but other detection means may also be used such an instrumental approaches based on mass spectrometry.

REST systems and procedures are the state of the art in terms of detection dog screening. REST combines traditional detection dog capabilities with leading biological and chemical science and is currently employed in the UK to screen environments for explosives. The system however has the potential for utilisation in the detection of many other substances such as drugs, and chemical and biological materials.

During the REST detection procedure a volume of air is drawn from a suspect environment through an adsorbent filter to capture vapours present in the air. The filter is later presented to a dog for analysis using a stand based system in a controlled environment. REST dogs are trained to indicate on extremely low concentrations of a substance captured on a filter. This complements other detection methods such as x-ray and nuclear techniques allowing, for example, larger cargo to be rapidly screened and has the advantage that it does not require the detection dog to have direct access to the cargo. The dog is able to work for longer because it is subject to less physical exertion than a 'free-running' search dog, and the stand-based system enables rigorous quality assurance and 'reward runs' by facilitating the presentation of 'positive' control samples to the dog. The REST system can be easily relocated, can enable rapid screening of a large number of enclosed environments such as vehicles, cargo containers or the like.

Training aids are required to train new detection dogs and to maintain confidence that existing dogs are working effectively. For example, training aids for dogs in accordance with the REST procedure must incorporate a REST adsorbent filter doped with a target substance. One method currently in use for the production of training aids, hereinafter referred to as the "fish tank method", comprises a chamber containing a substance from which an air sample can be drawn under laboratory conditions, wherein vapour or aerosol from the substance in the chamber impregnates the air. In order to capture the variety of scent characteristics in the impregnated air the air is drawn through or passed over a substrate, such as a filter. Another method, hereinafter referred to as the "simulated environment method", comprises a simulated cargo pallet, or other desired simulated environment, into which a substance is placed. The air is then similarly withdrawn from the simulated environment and drawn through or passed over a substrate as described above. The above practices ensure that at all times the substance for detection, which may be hazardous, remains in a controlled environment.

As used herein, training aid denotes a substrate comprising a quantity of a substance.

As used herein, substrate denotes a material that can retain a quantity of a substance, such as an adsorbent filter material.

As used herein, substance denotes a chemical or biological material in a liquid or solid form, which is capable of being vaporised or aerosolized at a temperature between 5° C. and 30° C. The substance may for example be an explosive.

As used herein, a real or genuine environment is the environment found at a genuine situation, for example the environment of a real cargo hold, or the environment of a real air terminal, as opposed to a simulated environment which as used herein denotes a fake or mock environment that seeks to emulate the characteristics of a real environment. A real or genuine environment will exhibit a multitude of natural scents in the air of such an environment, which are unlikely to be able to reproduced or emulated accurately in a simulated environment.

As use herein, an enclosed volume is an enclosed space to be screened for a substance. Examples of enclosed volumes include entire buildings (e.g. air terminals, cargo holds), a room in a building, shipping containers, vehicles (e.g. aircraft, ships), cargo freight and luggage.

The "fish tank method" utilises a small amount of substance in the production of training aids, but produces training aids which are not realistic because there are none of the background scents which would normally be present in a genuine/real environment, and laboratory scent characteristics are unintentionaly adsorbed onto the training aid; this can cue the dog and result in detection of the lab environment rather than the threat material.

The "simulated environment method" is designed to produce training aids that include background scent characteristics that may be associated with a particular genuine environment, allowing for a more realistic and supposedly effective means of training. This method also has a number of disadvantages. The "simulated environment method" requires use of a large quantity of substance, and thus is expensive and potentially poses a greater health risk to personnel, and further entails much time and expense in the location and construction of training terrains and simulated environments. Such simulated environments are often of questionable authenticity, consisting of a few key items thought to produce similar scent characteristics to those of the genuine environment they seek to emulate, and suffer the same issues associated with a prevailing background odour in the facility used to house the simulated environment as the "fish tank" method. Furthermore, the "simulated environment method" inherently comprises uncertainties in terms of the amount of substance consequently adsorbed onto a substrate and so variability in the quality of training aids produced.

The current methods thus potentially result in variable concentrations of substance, inconsistencies in quality, and incorporation of false environmental scents, such as laboratory air, all of which have been shown to lead to low detection rates, high false alarm rates and shortfalls in the ability of trained dogs to detect and discriminate. The element of repeatability of training aid production eludes all of the current state of the art, even that in a controlled laboratory environment.

There is therefore a requirement for a device or method that can produce training aids with repeatable concentrations of a substance, and concentrations of background scents from genuine environments, and further prevent inclusion of irrelevant scent characteristics.

The present invention thus generally aims to provide a means of controllably and reproducibly impregnating air with a substance, and consequently the substances scent characteristics, which is also preferably capable of incorporating background scent characteristics from genuine/real environments to enable the testing or training of detection means to evaluate and quantify the presence of the substance in an enclosed volume in a real environment, and in particular to enable production of training aids and quality assurance test items for use in canine-olfaction based security screening.

Accordingly, in a first aspect, the present invention provides a method for the impregnation of air with the vapour or aerosol of a substance in a repeatable and controlled manner to enable the testing or training of detection means to evaluate and quantify the presence of the substance in an enclosed volume in a real environment, comprising arranging for an airflow from an enclosed volume in a real environment to pass over a predetermined volume or predetermined surface area of substance supported within a conduit having an inlet and an outlet for passage of the airflow at a predetermined flow rate for a predetermined period of time thereby impregnating said air with said vapour or aerosol in a repeatable and controlled manner, and further arranging for delivery of said impregnated air to a means for detection of the substance.

One of the problems which the method of the first aspect addresses is that of preparing realistic and effective samples for testing and quantifying detection means to ensure that such means are capable of evaluating and quantifying the presence of the substance in an enclosed volume in a real environment, and especially the preparation of realistic and effective training aids and quality assurance test items for use in canine-olfaction based security screening. Previously, realistic samples could only be prepared by placing a realistic bulk quantity of contraband substance inside the enclosed volume, waiting for equilibration, and then extracting an air sample for analysis. The logistical cost and commercial unacceptability of this approach prohibits its widespread use. The present invention eliminates the need to invasively place a large quantity of bulk material inside the enclosed volume by means of a conduit that combines air from the enclosed volume with authentic vapours or aerosols from a small quantity of substance supported therein. This significantly reduces the cost and logistic burden of preparing training aids (for dogs or sensing algorithms) and quality assurance testing of detection means.

The method is in particular designed to test, train and/or calibrate detection means for detecting contraband substances, and to test the effectiveness of such detection means when the substance is encountered in the presence of other vapours or aerosols present in the air of a genuine environment. The advantage of the method over those in the art is that the substance is presented to the means for detection in a form it is most likely to be found in a real or genuine environment (i.e. mixed with vapours and/or aerosols from the genuine environment), rather than in a pure form, or alternatively in a form designed to mimic or simulate the mixture of vapours and/or aerosols present in a genuine environment.

The method of the first aspect is particularly designed to mix scent characteristics from a substance with scent characteristics present in the air extracted from an enclosed volume in a real environment prior to detection. The method provides the substance in a form it is likely to be encountered in a genuine environment, i.e. mixed with background scent characteristics from that genuine environment. Means for detection may be by an instrument requiring calibration; alternatively the means for detection may be a detection dog requiring training, via capture of the mixture of vapour/scent characteristics on a substrate. Until now, the possibility of taking a substance, particularly a hazardous substance, into a genuine environment in order to mix genuine environment scents with scent characteristics from a substance has been routinely dismissed as a dangerous and unduly expensive practice. As detailed above, the state of the art for producing training aids shares the central characteristic of keeping a substance and any genuine detection environment well and truly separate, at no point is the substance brought into the vicinity of a genuine environment, for example, actual cargo. The use of air from a genuine environment provides for the presentation of a substance to a detector in a form most likely to be encountered when detecting the substance in a genuine environment. The method provides more effective training aids for detection dog training.

The amount of substance required in the present method can be minimal thereby providing for a less expensive and safer means of mixing vapour and/or aerosol from a substance with air from a genuine environment than the state of the art. The mass, volume and surface area of substance may be varied, thereby enhancing the element of control in the method. The substance is most likely a chemical or other volatile substance, and may be an explosive.

Preferably, vapour or aerosol from the substance will be entrained at a temperature between 5° C. and 30° C. A substance such as an explosive compound may have a vapour pressure as low as $1 \times 10^{-5}$ Pa. The vapour pressure of explosive compounds may differ by a factor of 100 between these temperatures.

Delivery of impregnated air in accordance with the first aspect of the present invention may comprise adsorption of the impregnated airflow onto a substrate. Such substrate may comprise a filter, which may be of the kind currently prescribed by the REST method.

The method according to the first aspect of the present invention may be a method for producing training aids for detection dog training, and more particularly wherein the detection dog training is the REST procedure as outlined above.

The present invention thus also provides a method for producing a training aid for detection dog training, comprising arranging for an airflow from an enclosed volume in a real environment to pass over a predetermined volume or predetermined surface area of the substance supported within a conduit having an inlet and an outlet for passage of the airflow at a predetermined flow rate for a predetermined period of time thereby impregnating said air with the vapour or aerosol of said substance in a repeatable and controlled manner, and adsorbing said impregnated air onto a substrate, wherein the substrate comprising the substance is the training aid.

The methods according to the first aspect of the present invention arrange for a conduit to house the substance such that the airflow passes through the conduit and thereby over the substance, wherein vapour or aerosol from said substance impregnates the airflow. The conduit may be part of a device.

Accordingly, in a second aspect, the present invention provides a device for the impregnation of air with vapour or aerosol of a substance in a controllable manner to enable the testing or training of detection means to evaluate and quantify the presence of the substance in an enclosed volume in a real environment, comprising a conduit having an inlet and an outlet for passage of an airflow and a means for supporting a predetermined volume or predetermined surface area of substance within the conduit such that in use the air flowed through the device is impregnated with the vapour or aerosol of the substance.

The means for supporting a predetermined volume or predetermined surface area of substance contained within the device, and consequently the predetermined volume or predetermined surface area of substance itself, provides at least in part for the element of control in the impregnation. Further control is enabled by the dimensions of the conduit, and by controlling the rate of air flowing through the conduit.

In one embodiment, the conduit comprises two interconnecting flow channels, a first flow channel and a second flow channel, wherein the means for supporting the predetermined volume or predetermined surface area of substance is within the second flow channel, such that in use air entering the conduit is divided between the two flow channels, impregnated with the vapour or aerosol from the substance in the second flow channel, and then recombined prior to exiting the conduit.

The interconnecting flow channels enhance the element of control in the impregnation of air through division of the airflow in the device, with a controlled proportion of the airflow entering the second flow channel to contact the substance therein, while the rate of airflow exiting the device is substantially conserved.

The means for supporting a predetermined volume or predetermined surface area of substance may be a chamber, the dimensions of which can further enhance the element of control in the production of training aids. The production of vapour from a substance in a chamber of small volume will more rapidly reach a state of equilibrium. A device comprising a chamber of small volume can thus minimise the effect of any time variable in the production of training aids, such as the time that the substance is retained in the device prior to impregnation, or the time between production of each training aid, thus enabling consistency and control in training aid production, especially in the amount of substance adsorbing to a substrate. A chamber of small volume effectively removes the variable of the time lapse between each production.

The chamber may further comprise a central cylinder or recessed well of predetermined dimensions. The cylinder may be removable for ease of use and to enable the pre-preparation of a substance in a controlled environment prior to air extraction through the device, which may be of particular importance with volatile substances such as explosives which may pose a health and safety risk to personnel. Preparation in a controlled environment may also significantly reduce risks of cross contamination. The cylinder is preferably porous to allow air to contact the majority of the surface of a substance held therein. The chamber may comprise a mesh material for use with for example powdered or particulate substances, wherein the mesh is capable of containing the substance but which does not significantly restrict the airflow therethrough.

The dimensions of the first channel and second channel may be such that a certain percentage of airflow is drawn into the second flow channel, for example between about 1% and 25% of the airflow channeled into the device. The first and second flow channels may comprise a uniform diameter along their respective lengths; alternatively the first and second flow channels may comprise a variety of diameters along their respective lengths; further, one flow channel may comprise a variety of diameters along its respective length while the other may comprise a uniform diameter along its respective length. The applicant has found that variations in diameter along a flow channel can be utilised to control the ratio of airflow through the first and second flow channels, thereby providing further means to control impregnation and consequently the various possible concentration outputs of the device. The applicant has found that the dimensions of the first and second flow channels can provide control over the rate of airflow through the first and second flow channels. For example, having a broader diameter of the first flow channel at the position of a junction with the second flow channel has the effect of reducing the airflow velocity, and consequently encouraging airflow into the second flow channel. Furthermore, a reduction in the diameter of the first flow channel between the junctions of the first flow channel with the second flow channel also encourages this flow diversion. The dimensions may be such that the second flow channel has a diameter of 13 mm. The first flow channel diameter may start at 9.5 mm, expand to 13.5 mm, restrict to 9.5 mm, expand to 13.5 mm, and restrict to 9.5 mm. In such an embodiment, the second flow channel may be connected or joined to the first flow channel at the two 13.5 mm diameter sections of the first flow channel. When used with a rate of airflow of 60 $L \cdot min^{-1}$, these dimensions provide for a rate of airflow through the second flow channel of approximately 14 $L \cdot min^{-1}$.

Control of the airflow rates through the chamber could be provided by use of an adjustable flow restrictor, an object comprising a plurality of holes of various diameters, arranged in a flow channel at the outlet side of the chamber. Such an object could be capable of movement through the flow channel in order to select a desired diameter.

A further embodiment of the device according to the second aspect of the present invention may comprise dimensions such to accommodate an airflow compatible with the REST method and approved equipment for the production of detection dog training aids. At present, for example, the REST method and equipment is designed to utilise an airflow rate of 60 $L min^{-1}$.

The conduit provides for control and accuracy in airflow impregnation. The conduit can also enable the substance to be contained, which is especially important when using hazardous substances.

Modifications of the methods of use may allow for controllable variation of training aids produced i.e. in the concentration of substance adsorbed onto a training aid substrate. The flow rate of the air flowing over the substance may be reduced or increased to provide for a corresponding stronger or weaker concentration of training sample, as may the period that air is flowed over the substance. This may be combined with varying the volume or surface area of the substance and/or variations in temperature which may also affect the rate of airflow impregnation. The above variables, when controlled, provide for a calculable, wide range of air impregnation rates, and in relation to detection dog training provide for calculable adsorbed vapour masses, thereby providing for the element of repeatability that has so alluded the prior art.

The present invention will now be described with reference to the following non-limiting examples and figures in which.

FIG. 8 is a graph showing the stability of emissions of Substance B on three separate days from device V2a. The error bars represent one standard deviation; and FIG. 9 is a graph showing stability of emissions of Substance B on three separate days from device V2b. The error bars represent one standard deviation.

Figure 10:
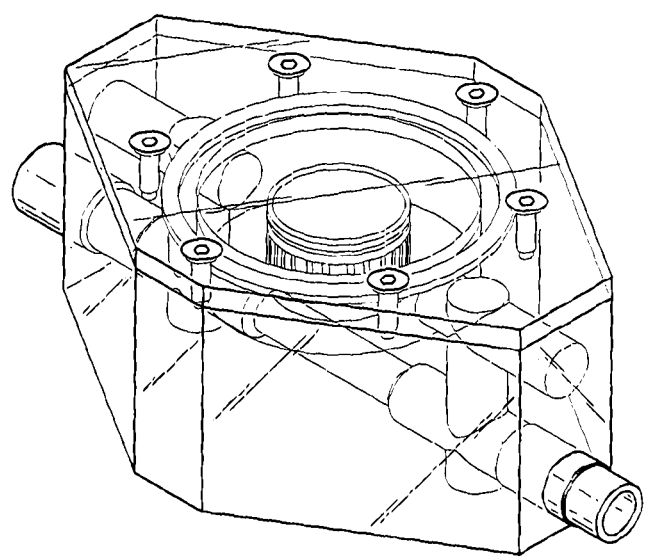

FIG. 10 is a drawing of one embodiment of the device.

EXAMPLES

A device has been produced to enable production of training aids having a range of concentrations of a substance to train detection dogs. The device is required to produce training aids of concentrations that are comparable to that potentially encountered by sampling air from an enclosed volume in a genuine environment.

Figure 1:
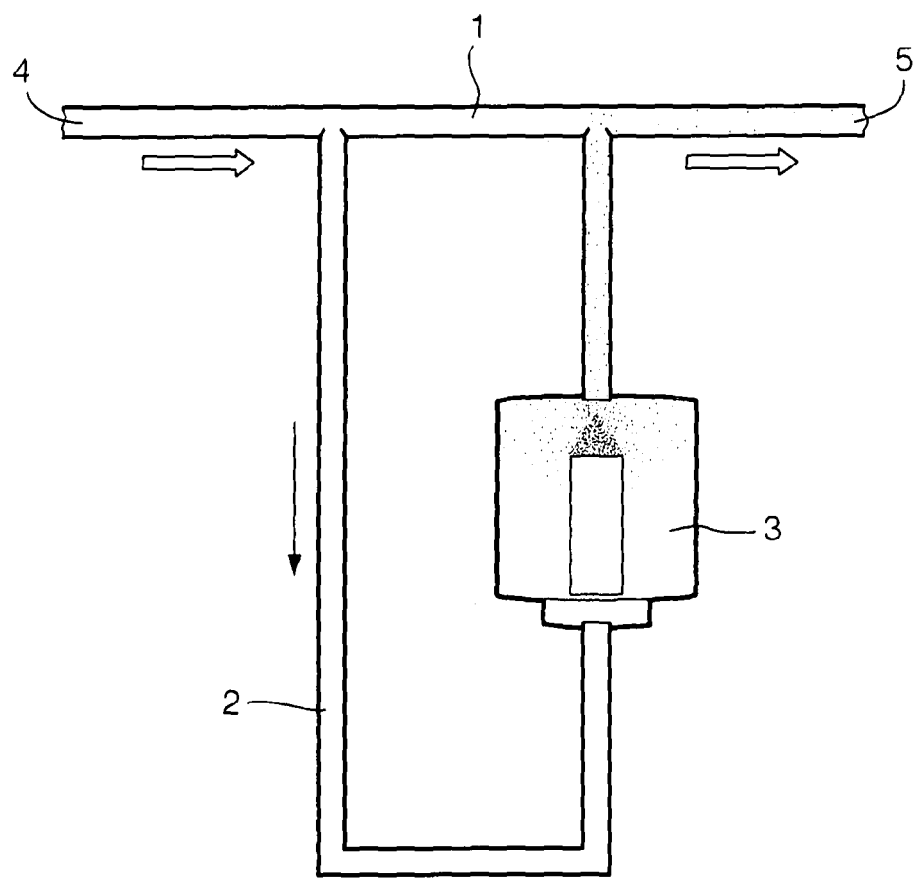
FIG. 1 is a Computational Fluid Dynamics (CFD) image showing one embodiment of a device of the first aspect (V1)

Having regard to FIG. 1, the device comprises a first flow channel 1, a second flow channel 2, a chamber 3 for retaining a substance, an inlet 4 and an outlet 5. Air can be drawn through the device by use of a pump, such as the REST pump, connected to outlet 5. In the case of the REST method, a REST filter would also be located at outlet 5 Tubing (not shown) connected to inlet 4 can be inserted into a genuine environment, such as cargo. The majority of the sampled air passes through first flow channel 1 with a smaller proportion diverting along second flow channel 2 and through chamber 3. The proportion of air that passes through chamber 3 is controlled by the dimensions of the first flow channel 1, the second flow channel 2 and chamber 3 itself.

Figure 2A:
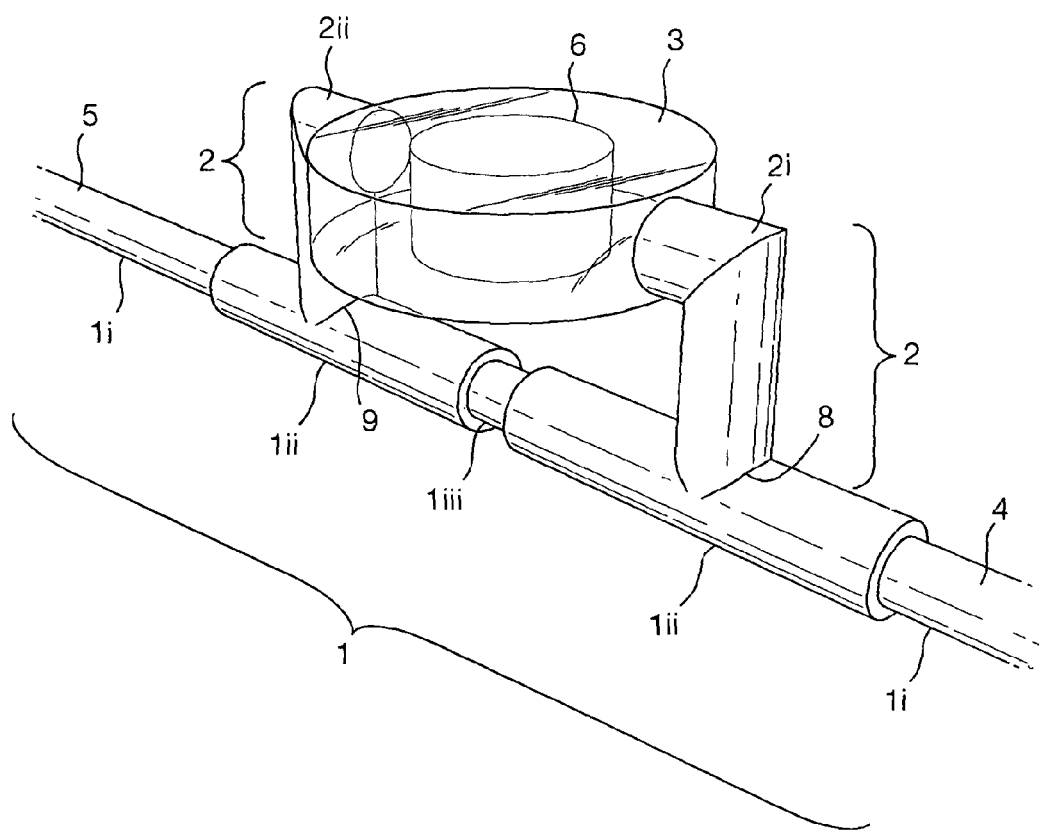
FIG. 2a is an image of the CFD model of a second embodiment of the device (V2a)
Figure 2B:
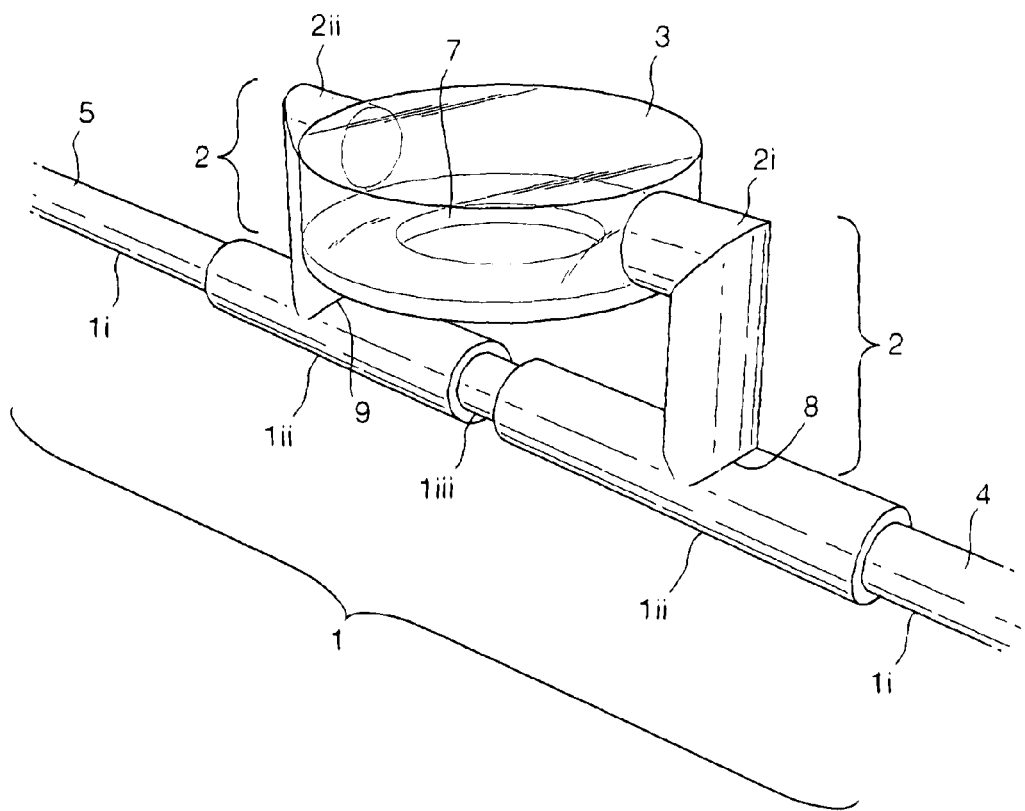
FIG. 2b is an image of the CFD model of a third embodiment of the device (V2b)

Having regard to FIGS. 2a and 2b, two devices (V2a and V2b) were produced, one where the substance could be retained in chamber 3 within a porous cylinder 6 (V2a) and the other where the substance could be retained in chamber 3 within a recessed well 7 (V2b).

CFD modelling was used to refine the dimensions of the designs. In particular refinements to the diameter of the second flow channel 2 were investigated, especially sections 2i and 2ii of the second flow channel, either side of chamber 3. Refinements to the diameter of the first flow channel 1 were also investigated, especially utilisation of variable diameters 1i, 1ii and 1iii. Other potential refinements included angling sections 2i and 2ii.

It was found that reducing the diameter of second flow channel 2, in particular section 2ii on the outlet side of the device, with respect to the diameter of the first flow channel 1 and/or section 2i, could reduce the rate of airflow through second flow channel 2 and chamber 3, achieving control of the amount of substance vapour exiting the device whilst maintaining the overall flow rate through the device, and consequently leading to more consistent sampling.

Having regard to FIGS. 2a and 2b, devices at least partially optimised for use with the REST method and instrumentation had the following dimensions. The second flow channel 2 has a diameter of 13 mm throughout. The first flow channel 1 has a variety of diameters along its length, with sections 1i and 1iii of 9.5 mm, and sections 1ii of 13.5 mm. It was observed that the wider diameter of section 1ii of 13.5 mm, situated at junction 8 and junction 9 between the first flow channel 1 and second flow channel 2, had the effect of reducing the airflow rate through that section of first flow channel 1, with the further effect that the airflow has a greater chance of diverting along the second flow channel 2, and so increases the airflow through chamber 3. Having regard to FIG. 2a, at an overall flow rate through the device of 60 L·min$^{-1}$, a CFD model predicted that the flow rate through chamber 3 of device V2a would be 13.9 L·min$^{-1}$ and that through chamber 3 of device V2b would be 14.3 L·min$^{-1}$. This flow rate could then be adjusted in a controllable manner though the utilisation of an adjustable flow restrictor located in section 2ii of second flow channel 2.

An adjustable flow restrictor may comprise a length of acrylic 14 mm by 130 mm, with holes of a variety of diameters centrally aligned along its length. The adjustable flow restrictor may interrupt the path of a flow channel across the flow channel's diameter, the adjustable flow restrictor at all times engaged with the walls of the flow channel, such that no air escapes the device. Air can then be forced through the chosen hole within the adjustable flow restrictor. Such a restrictor may provide for the restriction of, for example, a 13 mm diameter flow channel at a point after the chamber outlet (and, in a multiple channel embodiment, prior to rejoining the other flow channel) to, for example, 1.63 mm in diameter, and so increase the pressure and decrease the rate of airflow through the chamber, thus providing greater control over air impregnation. The effects of adjustments to the diameter of section 2ii, which could be provided by a flow restrictor, are shown in Table 2.

Having regard to FIG. 2a (V2a), cylinder 6 has a 30 mm diameter and is 15 mm high V2a has the advantage over V2b that the cylinder is self contained and so could easily be removed for storage etc. Having regard to FIG. 2b (V2b), recessed well 7 has a 30 mm diameter and is 10 mm deep Device V2a would be easier to use operationally because substances could be pre-prepared in the cylinder 6 in a controlled environment and then be placed in the device with a minimum of difficulty by the user. Sample chamber 3 in both V2a and V2b is 60 mm diameter and 15 mm deep. Such dimensions advantageously provide a chamber of small volume which is capable of enhancing consistency and control in the production of training aids. A device comprising a chamber of small volume was shown to effectively eradicate the effect of certain time variables in the production of training aids, such as the time that the substance is retained in the device prior to impregnation, or the time between production of each training aid. Such a small chamber is also capable of essentially overcoming variabilities in the vapour pressure of substances due to fluctuations of temperature, since the production of vapour from a substance will rapidly reach a state of equilibrium, consequently minimising the effect of any such variability.

Figure 3:
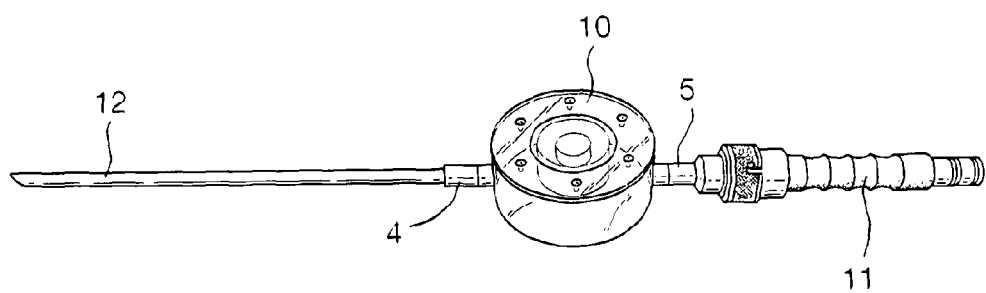
FIG. 3 is a photograph of an embodiment of the device (V2a) connected to the REST pump and filter holder, and a polyethene tip for insertion into the genuine environment.

Having regard to FIG. 3, device 10 is illustrated connected to the REST pump and filter holder 11, and polyethene tip 12. The device 10 includes threaded fittings at inlet 4 and outlet 5 for simple removal/fitting of 11 and 12.

The applicant has observed that the material the device is made from may have an effect upon its ability to impregnate air with only scent characteristics from a selected genuine, environment. Following analysis of a range of materials, the limited scent characteristics of an inert polymer such as acrylic were found to have the least detrimental effect in producing training aids.

A mesh can be incorporated into the chamber 3 in order to enable use of the device with powdered or particulate substances. The mesh would need to be fine enough to contain the powder but coarse enough so as to not restrict the flow of the vapour significantly.

A range of different meshes (from Goodfellow, Huntingdon, UK) were tested and the coarsest was found to contain the powder. The mesh had the following properties:
Material—Polyethylene terephthalate
Nominal aperture—100 μm
Monofilament diameter—70 μm
Threads/cm—55
Open area—33%
Plain weave mesh Experiments were conducted to assess the impact of the mesh's inclusion in device V2a, arranged around the inner surface of the porous cylinder, and V2b, fixed over the opening of the recessed well, upon impregnation and thereby adsorption onto a substrate. Having regard to FIG. 2a, the inside of the cylinder 6 was lined with a single sheet of plastic mesh and rolled into a cylinder to enable retention of a substance. Having regard to FIG. 2b, the opening of well 7 was covered with the plastic mesh. The variation in output was however minimal, with a reduction of only 2.4%.

Two explosive substances were tested in devices V2a and V2b, substance A and substance B, with dimensions and masses indicated in Table 1.

TABLE 1

Substances evaluated using devices V2a and V2b

| Probe | Substance A | | Substance B | |
|---|---|---|---|---|
| | Dimensions dia × h (mm) | mass (g) | Dimensions dia × h (mm) | mass (g) |
| V2a | 25 × 15 | 9.6 | 23 × 15 | 7.5 |
| V2b | 25 × 7 | 6.1 | 23 × 7 | 3.9 |

Having regard to FIG. 3, laboratory air was drawn through the device by the REST pump in the conventional manner for 10 s, 30 s, 60 s, 120 s and 180 s, and impacted on a REST filter. During experiments air was sampled orthogonally from the main airflow using a personal air sampler (Universal model, SKC) to draw vapours onto a Tenax™ trap which was then analysed by thermal desorption gas chromatography mass spectrometry (TD GC-MS) A limitation of the technique was that it was only possible to sample 2 L min$^{-1}$ from a total airflow of 60 L min$^{-1}$. Thus the technique was limited to substances which release a large amount of vapour. The ratio of vapour pressures of some example compounds over a temperature range 5° C. to 30° C. were found to be up to 100.

Measurements for each substance and sampling time were repeated five times. A comparison was also made on the day to day stability of the emissions from a single substance by comparing the levels produced on three different days (1, 12 and 22 days after placement of sample in the device) at similar ambient temperatures.

Cylinder 6 in device V2a was found to present a larger surface area of substance to the airflow and consequently produced higher levels of target vapour than recessed well 7 in device V2b.

Substance A

Figure 4:
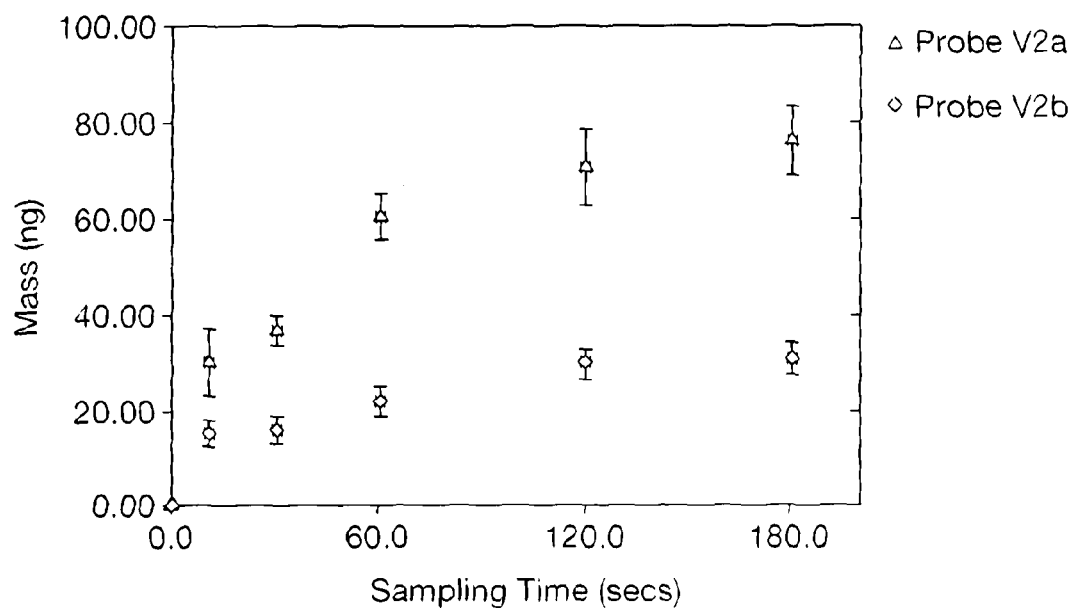
FIG. 4 is a graph showing the effect of sampling time on the emission of Substance A from devices V2a and V2b. The error bars represent one standard deviation.

The effects of sampling time of 10, 30, 60, 120 and 180 seconds on the amount of target vapour produced by both devices V2a and V2b are shown in FIG. 4

All data points recorded represent one thirtieth of the total vapour that has impregnated the airflow. The amounts produced at 60 seconds sampling time from device V2a (approximately 60 ng×30=1800 ng) are similar to the levels provided by the "fish tank method" (approximately 524 ng×10/4=1310 ng, to convert from a 2 L·min$^{-1}$ sample collected for 2 min to a 60 L·min-$^{-1}$ sample collected for 10 seconds). Device V2b also produced approximately the same amount of vapour as that of the "fish tank method".

Figure 5:
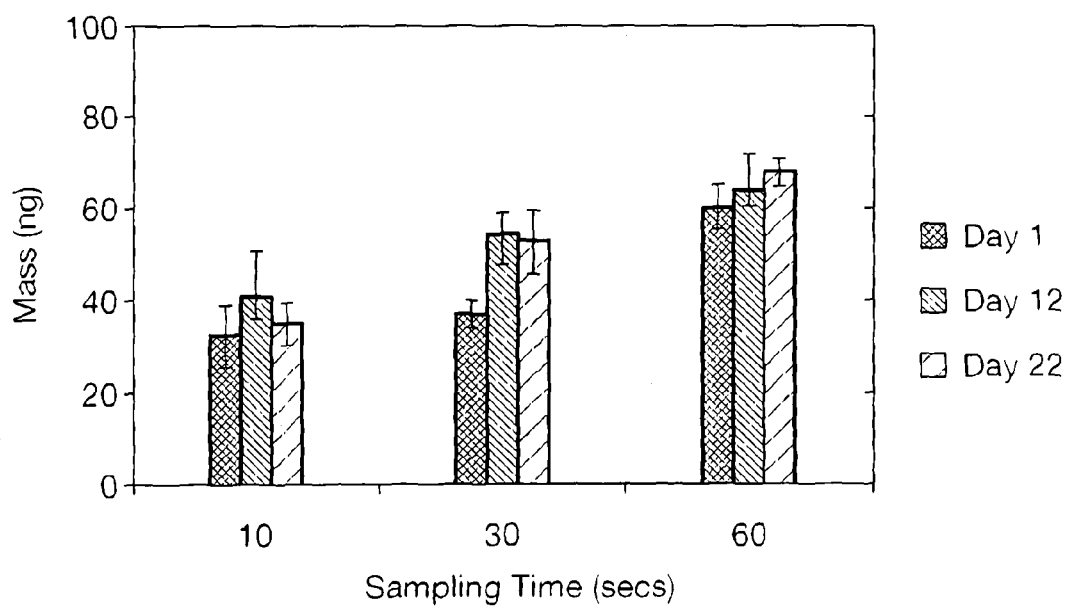
FIG. 5 is a graph showing stability of emissions on three separate days from device V2a. The error bars represent one standard deviation.
Figure 6:
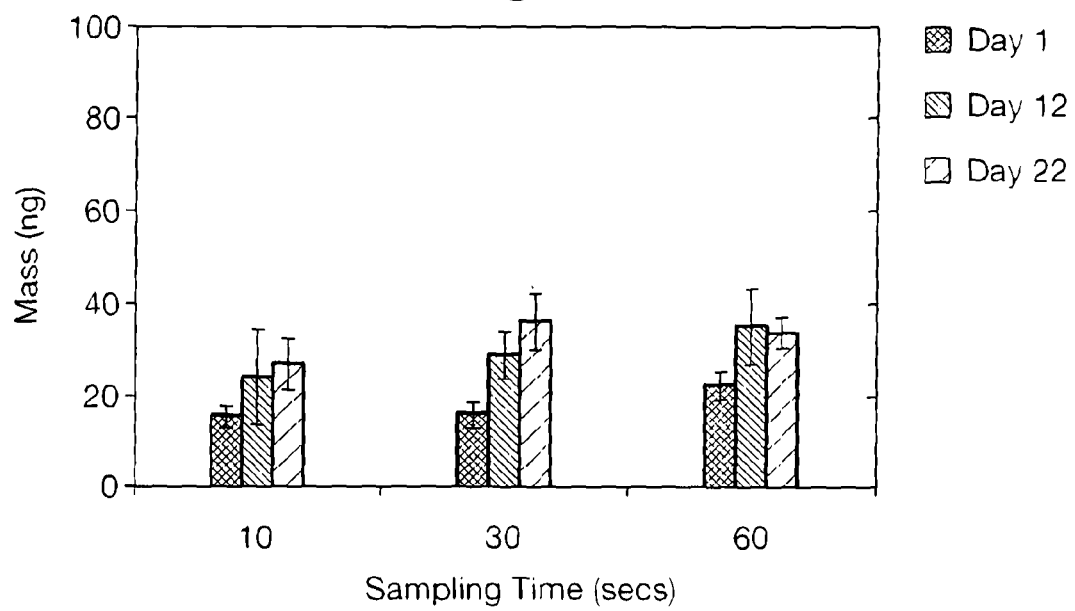
FIG. 6 is a graph showing stability of emissions on three separate days from device V2b. The error bars represent one standard deviation.

A demonstration of the stability of emissions from substance A produced from device V2a and device V2b on 1, 12 and 22 days after placement of the substance is shown in FIGS. 5 and 6 respectively.

Substance B

Figure 7:
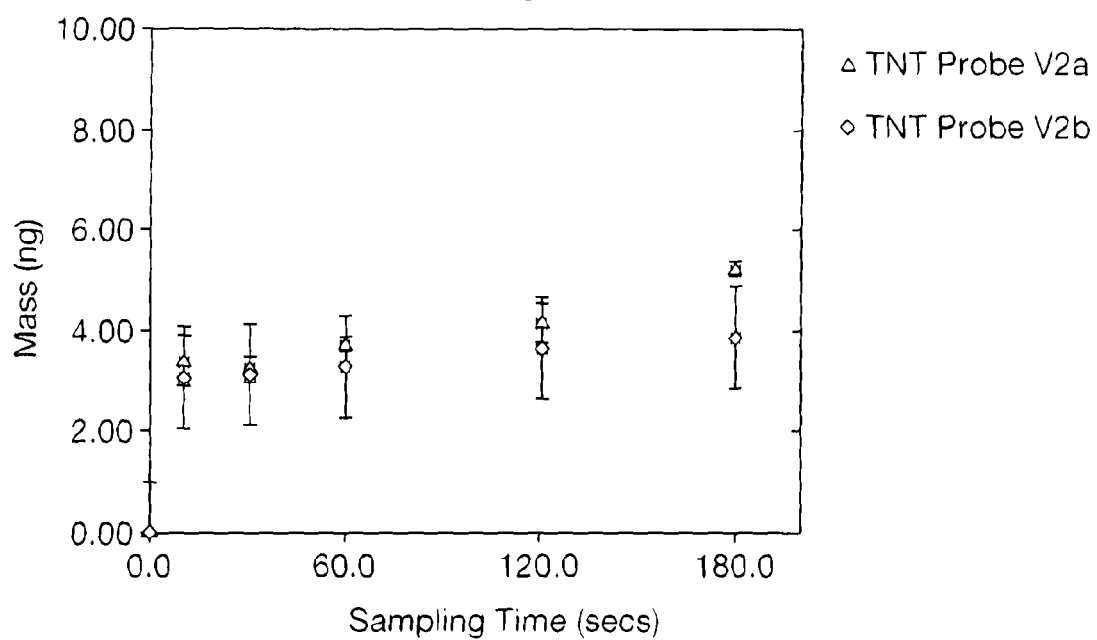
FIG. 7 is a graph showing the effect of sampling time on the emission of Substance B from devices V2a and V2b. The error bars represent one standard deviation.

The effect of sampling time on the amount of Substance B impregnating the airflow from device V2a and V2b are shown in FIG. 7.

The long term stability of emissions of the target vapour for substance B from device V2a and V2b on 1, 12 and 22 days after placement of the substance in the device was monitored with sampling times of 10 s, 30 s and 60 s shown in FIGS. 8 and 9 respectively.

Control of Sample Concentration

Having regard to FIG. 2a, following the demonstration that the device was producing sample concentrations at the upper end of the required range, CFD was used to assess how restricting the diameter of second flow channel 2 and varying sample times could reduce the amount of vapour output and investigate to what degree the output could be regulated. Table 2 shows the results from the CFD models. The restricted diameter in this instance was in section 2ii of the device, i.e. in the second flow channel subsequent to the outlet to the chamber.

TABLE 2

Mass of vapour output from the device V2a for two sample times and five section 2ii diameters.

| Chamber outlet diameter (mm) | Second flow channel flow rate (L · min$^{-1}$) | Mass samples after | |
|---|---|---|---|
| | | 30 seconds (ng) | 300 seconds (ng) |
| 13.00 | 14.4 | 332 | 3336 |
| 9.75 | 13.3 | 317 | 3185 |
| 6.50 | 8.8 | 238 | 2397 |

TABLE 2-continued

Mass of vapour output from the device V2a for two sample times and five section 2ii diameters.

| Chamber outlet diameter (mm) | Second flow channel flow rate ($L \cdot min^{-1}$) | Mass samples after 30 seconds (ng) | 300 seconds (ng) |
|---|---|---|---|
| 3.25 | 2.9 | 153 | 1547 |
| 1.63 | 0.8 | 83 | 869 |

By restricting the diameter of section 2*ii*, the flow could be reduced by a factor of 28 but the mass of sample output only reduced by approximately 4. Additional ways to increase the concentration range include:

1. Varying the mass of substance in the chamber, though too small a mass of substance could be highly susceptible to drying out and so the consistency of the samples could be compromised.

2. Varying the type of mesh in the chamber to slow the vapour transfer into the airflow.

Device V2*a* can produce training aids that have a mass of vapour that is comparable to that produced with the fish tank method. Experiments have confirmed that the device is capable of delivering reproducible quantities of the vapour associated with an explosive substance. Device V2*a*, in which the substance is contained in a cylinder, produced consistently higher levels of target vapour than device V2*b*. The day-to-day stability of emissions from the probe as indicated by the standard deviation was good. Tests with explosives showed a linear relationship between sample time and mass output for shorter sampling time (60 seconds or less) but at longer times the emissions reduced.

The invention claimed is:

1. A method for the impregnation of air with the vapour or aerosol of a substance in a repeatable and controlled manner to enable the testing or training of means for detecting to evaluate and quantify the presence of the substance in an enclosed volume in a real environment, comprising arranging for an airflow from said enclosed volume in said real environment to pass over a predetermined volume or predetermined surface area of the substance supported within a conduit having an inlet and an outlet for passage of the airflow at a predetermined flow rate for a predetermined period of time thereby impregnating air of said airflow with said vapour or aerosol of said substance in a repeatable and controlled manner, and further arranging for delivery of said impregnated air to said means for detecting the substance, wherein said real environment is the environment found at a real situation, as opposed to a simulated environment which is a fake or mock environment that seeks to emulate the characteristics of said real environment.

2. The method according to claim 1, wherein the substance comprises an explosive.

3. The method according to claim 1, wherein delivery of impregnated air comprises adsorption of said impregnated airflow onto a substrate.

4. The method according to claim 1, wherein said real environment is a cargo hold, and the enclosed volume is cargo.

5. The method according to claim 1, wherein the conduit is within a device, and the conduit comprises a means for supporting a predetermined volume or predetermined surface area of substance within the conduit such that in use the air flowed through the device is impregnated with the vapour or aerosol of the substance.

6. The method according to claim 5, wherein said conduit comprises two interconnecting flow channels, a first and second flow channel, wherein the means for supporting the predetermined volume or predetermined surface area of substance is within the second flow channel, such that in use air entering the conduit is divided between the two flow channels, impregnated with the vapour or aerosol of the substance in the second flow channel, and then recombined prior to exiting the conduit.

7. The method according to claim 5, wherein the means for supporting a predetermined volume or predetermined surface area of substance comprises a chamber.

8. The method according to claim 7, wherein said chamber comprises a removable cylinder.

9. The method according to claim 7, wherein said chamber further comprises a mesh material wherein said mesh material is capable of containing a substance but which does not restrict the airflow significantly.

10. The method according to claim 5, comprising dimensions such to accommodate an airflow compatible with the use of REST approved equipment for the production of detection dog training aids.

11. The method according to claim 1, for the production of training aids for detection dog training, wherein the detection dog training is the REST procedure.

12. A method for producing a training aid for detection dog training, comprising arranging for an airflow from an enclosed volume in a real environment to pass over a predetermined volume or predetermined surface area of a substance supported within a conduit having an inlet and an outlet for passage of the airflow at a predetermined flow rate for a predetermined period of time thereby impregnating air of said airflow with a vapour or aerosol of said substance in a repeatable and controlled manner, and adsorbing said impregnated air onto a substrate, wherein the substrate comprising the substance is the training aid, and wherein said real environment is the environment found at a real situation, as opposed to a simulated environment which is a fake or mock environment that seeks to emulate the characteristics of said real environment.

* * * * *